(12) United States Patent
Bakker (10) Patent No.: US 7,899,636 B2
(45) Date of Patent: Mar. 1, 2011

(54) CALIBRATION OF OPTICAL ANALYSIS MAKING USE OF MULTIVARIATE OPTICAL ELEMENTS

(75) Inventor: Bernardus Leonardus Gerardus Bakker, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 259 days.

(21) Appl. No.: 11/721,368

(22) PCT Filed: Dec. 12, 2005

(86) PCT No.: PCT/IB2005/054176
§ 371 (c)(1),
(2), (4) Date: Sep. 29, 2009

(87) PCT Pub. No.: WO2006/064446
PCT Pub. Date: Jun. 22, 2006

(65) Prior Publication Data
US 2010/0042348 A1 Feb. 18, 2010

(30) Foreign Application Priority Data
Dec. 15, 2004 (EP) .................. 04106584

(51) Int. Cl.
*G06F 19/00* (2006.01)
*G01J 3/00* (2006.01)
(52) U.S. Cl. .................. 702/85; 356/300
(58) Field of Classification Search .......... 702/85; 356/300
See application file for complete search history.

(56) References Cited

U.S. PATENT DOCUMENTS

| 2,837,959 A * | 6/1958 | Saunderson et al. .......... 356/329 |
| 5,553,616 A | 9/1996 | Ham |
| 6,044,285 A | 3/2000 | Chaiken |
| 6,198,531 B1 | 3/2001 | Myrick |
| 6,205,354 B1 | 3/2001 | Gellermann |
| 6,721,583 B1 | 4/2004 | Durkin |
| 2001/0034478 A1 | 10/2001 | Lambert |
| 2003/0023170 A1 | 1/2003 | Gardner |
| 2003/0176777 A1 | 9/2003 | Muller-Dethlefs |
| 2008/0309930 A1 * | 12/2008 | Rensen .................. 356/300 |

FOREIGN PATENT DOCUMENTS

| EP | 1089146 A2 | 4/2001 |
| WO | 2002057759 A1 | 7/2002 |
| WO | 2004008090 A1 | 1/2004 |

* cited by examiner

*Primary Examiner* — Bryan Bui (57) ABSTRACT

A method of calibrating an optical analysis system uses multivariate optical signal analysis. The method includes determining a parameter of a reference sample, and comparing the actually determined parameter with a reference parameter that represents a precise and real property of the reference sample. Based on the comparison, a calibration value is determined that is applicable to perform a calibration of the optical analysis system with respect to at least one compound or analyte of the reference sample. Parameters and reference parameters of a reference sample may refer to a concentration of an analyte dissolved in the sample, or to spectroscopic background signals that have to be taken into account when performing a spectral analysis based on optical signals obtained from the reference sample. Analyte-specific reference data is stored in a calibration unit of the optical analysis system and allows a high degree of automation of the calibration process.

13 Claims, 7 Drawing Sheets

| System parameter | Value |
|---|---|
| detector noise | 0.02 % |
| inherent noise | 0.2 % |

60 — 66 (detector noise) — 68 (inherent noise)

| Component | calibration value |
|---|---|
| A | 0.02 |
| B | -0.024 |
| C | -002 |

64

| Sample Nr. | Compound A | Compound B | Compound C | background level |
|---|---|---|---|---|
| 1 | 0.05% | 0.02% | 5 % | 40 % |
| 2 | 10 % | 0.00 % | 20 % | 20 % |

CALIBRATION OF OPTICAL ANALYSIS MAKING USE OF MULTIVARIATE OPTICAL ELEMENTS

BACKGROUND OF THE PRESENT SYSTEM

The present invention relates to the field of optical spectroscopy and in particular without limitation to optical spectroscopy utilizing multivariate optical means for spectral analysis.

Spectroscopic techniques are widely used for determination of the composition of a substance. By spectrally analyzing an optical signal, i.e. a spectroscopic optical signal, the concentration of a particular compound or analyte of the substance can be precisely determined. The concentration of a particular analyte or compound is typically given by an amplitude of a principal component of an optical signal.

U.S. Pat. No. 6,198,531 B1 discloses an embodiment of an optical analysis system for determining an amplitude of a principal component of an optical signal. The known optical analysis system is part of a spectroscopic analysis system suited for, e.g., analyzing which compounds are comprised at which concentrations in a sample. It is well known that light interacting with the sample carries away information about the compounds and their concentrations. The underlying physical processes are exploited in optical spectroscopic techniques in which light of a light source such as, e.g., a laser, a lamp or light emitting diode is directed to the sample for generating an optical signal that carries this information.

For example, light may be absorbed by the sample. Alternatively or in addition, light of a known wavelength may interact with the sample and thereby generate light at a different wavelength due to, e.g. a Raman process. The transmitted and/or generated light then constitutes the optical signal which may also be referred to as the spectrum. The relative intensity of the optical signal as a function of the wavelength is then indicative of the compounds comprised in the sample and their concentrations.

To identify the compounds comprised in the sample and to determine their concentrations the optical signal has to be analyzed. In the known optical analysis system the optical signal is analyzed by dedicated hardware comprising an optical filter. This optical filter has a transmission which depends on the wavelength, i.e. it is designed to weight the optical signal by a spectral weighting function which is given by the wavelength-dependent transmission. The spectral weighting function is chosen such that the total intensity of the weighted optical signal, i.e. of the light transmitted by the filter, is directly proportional to the concentration of a particular compound. Such an optical filter is also denoted a multivariate optical element (MOE), that may be implemented in transmission or reflection geometry. This intensity can then be conveniently detected by a detector such as, e.g., a photodiode. For every compound a dedicated optical filter with a characteristic spectral weighting function is used. The optical filter may be, e.g., an interference filter having a transmission constituting the desired weighting function.

Typically, the principal component comprises a positive part and a negative part. Therefore, a part of the optical signal is directed to a first filter which weights the optical signal by a first spectral weighting function corresponding to the positive part of the principal component, and a further part of the optical signal is directed to a second filter which weights the optical signal by a second spectral weighting function corresponding to the negative part of the principal component. The light transmitted by the first and second filters is then separately detected by a first and a second detector, respectively. The two signals obtained by the two detectors are then subtracted, resulting in a signal with an amplitude corresponding to the concentration of a dedicated compound of the sample.

In this way, instead of the entire spectrum, only a single signal that is proportional to a specific compound of the sample is detected. Hence, a rather expensive charge coupled device (CCD) camera can be effectively replaced by low-cost light sensitive detectors, such as e.g. semiconductor-based photodiodes. However, by means of such a multivariate optical analysis only two signals, namely the positive and the negative parts of the principal component, are obtained. They are representative of the spectroscopic signal itself and also correspond to a non-negligible background signal. For a precise and reliable determination of the concentration of a compound or analyte of the investigated substance, the entire spectroscopic system has to be correctly calibrated. Hence, the correlation between the detected principal component and a corresponding concentration has to be scaled properly.

In many spectroscopic analysis systems elastically scattered radiation as well as dark current of the detector may give rise to appreciable background signals that are superimposed on the intrinsic spectroscopic signal. Typically, spectroscopic signals that have to be analyzed feature relatively narrow peaks in the spectrum compared to the broadband fluorescence or dark current background. Generally, a reliable and sufficient spectroscopic analysis requires effective elimination of broadband background signals.

This can for example be provided by filtering of slowly varying signal components of a spectrum. However, by making use of MOEs only a single signal rather than the entire spectrum is detected. Consequently, a filtering of slowly varying spectral components cannot be performed in a straightforward way. However, background compensation is a necessary step of spectroscopic signal analysis and it also has to be applied on spectroscopic analysis based on multivariate optical analysis.

The advantages of a background compensation scheme are obvious, when for example the background is subject to modifications that might easily occur in the framework of spectroscopic analysis of biological tissue. In particular, when spectroscopic analysis is applied to a variety of different biological tissues featuring different optical properties, a fluorescence background may strongly depend on the type of the biological tissue. Moreover, other effects like scattering of light in a light guiding arrangement providing transmission of collected optical signals to a spectroscopic analysis system may also have a major impact on the background level. Also, when the background is non uniform, i.e. the fluorescence or dark current is not uniform over a large spectral range, subtracting a constant fluorescence and dark current background would falsify the spectroscopic signal to a large extent.

SUMMARY OF THE PRESENT SYSTEM

The present invention therefore aims to provide reliable and precise calibration of an optical analysis system including background correction of an optical spectrum that is subject to analysis by means of multivariate optical means.

The present invention provides a method of calibrating an optical analysis system that is adapted to determine an amplitude of the principal component of an optical signal by making use of a multivariate optical element (MOE) and a detector that is preferably implemented as a photodiode. The inventive calibration method comprises determination of at least one principal component of at least one optical signal that is obtained from at least a first reference sample. Based on the determined principal component at least a first parameter is derived that is representative of at least one property of the first reference sample. The obtained first parameter is then compared with a first reference parameter of the first reference sample and by making use of this comparison at least a first calibration value for the at least first parameter is determined. This at least first calibration value is applicable for calibrating the optical analysis system.

The optical signal that is obtained from the at least first reference sample typically comprises a spectrum of the reference sample that can be obtained when the at least first reference sample is exposed to an excitation radiation generated by e.g. the optical analysis system. The excitation radiation is typically generated by means of a laser light source. Typically, the optical signal comprises radiation that has been subject to inelastic scattering and that features a frequency shift with respect to the excitation radiation and further comprises a broadband fluorescence background. The principal component of the at least one optical signal is determined by means of the multivariate optical element and the detector. The MOE is typically implemented by means of a dispersive optical element in combination with a filter element having a spatial transmission function and thus provide a spectral weighting of the at least one optical signal.

The magnitude of the principal component or the amplitudes of the positive and negative parts of the principal component are directly indicative of a distinct property of the reference sample, like a concentration of a particular compound or analyte. The at least first parameter being derived by making use of the at least one principal component may therefore represent the concentration of a compound of the reference sample as it is determined by the optical analysis system. The at least first reference parameter in contrast represents the corresponding actual and correct magnitude of the at least first parameter of the reference sample. If the first parameter determined by the optical analysis system clearly deviates from the first reference parameter, the method determines a corresponding calibration value that can be used for mapping and transferring the measured parameter to the actual and precise reference parameter.

The reference parameter may be obtained by means of a more sophisticated and elaborate spectral analysis of the reference sample or by means of a well defined production of the reference sample. For instance, if the optical analysis system and its multivariate optical element are dedicated for measuring e.g. the concentration of glucose in an aqueous liquid, the reference sample may be designed by dissolving a certain well-known amount of glucose in an aqueous solvent.

The method of determining calibration values is applicable to several reference samples in a variety of different ways. Since a reference sample may comprise more than one compound or analyte, a single reference sample can be used to determine several principal components of an optical signal by applying various multivariate optical elements or by reconfiguring the MOE of the optical analysis system. In this way a variety of parameters can be obtained from a single reference sample that are comparable with corresponding well-known reference parameters of the reference sample. Consequently, a whole variety of calibration values can be obtained that allow to calibrate the optical analysis system with respect to various compounds or analytes. Also a whole variety of reference samples can be subsequently analyzed for calibration of the optical analysis system. Various reference samples can either be used for obtaining calibration values for various compounds or analytes or only for a few limited compounds or analytes, e.g. only one distinct analyte or compound. For instance, by making use of a variety of different reference samples, a variety of calibration values can be obtained that are all applicable for calibrating the optical analysis system with respect to a single analyte or compound. In this way a distribution of a set of calibration values can be used to generate a mean calibration value that allows to compensate for the statistical spread of a set of calibration values related to a common analyte.

According to a preferred embodiment of the invention, the at least first parameter and the at least first reference parameter of the reference sample are representative of a concentration of at least one compound of a substance that is located inside a volume of interest of the reference sample. Further, the at least one optical signal that is obtained from the volume of interest of the reference sample is representative of a spectroscopic signal and typically comprises a spectrum carrying information of the composition of the substance. Here, the first parameter may be obtained and derived from inelastically scattered radiation that stems from e.g. a Raman process taking place inside the volume of interest.

Moreover, parameters obtained from a reference sample may not only be related to concentrations of dedicated compounds or analytes of a substance of the reference sample but may also relate to environmental acquisition conditions and various internal structures of the reference samples.

According to a further preferred embodiment of the invention, the at least first parameter and the at least first reference parameter are representative of a portion of the at least one optical signal that is due to inelastic scattering of optical radiation inside the at least first reference sample. This allows to classify and to calibrate the optical analysis system with respect to spectroscopic signals obtained from the reference sample. Moreover, the at least one optical signal might also be due to elastic scattering of optical radiation inside the reference sample and may therefore represent e.g. a broadband fluorescence background of acquired optical signals. In this case, the reference parameter being representative of background noise of the reference sample, may be obtained and determined by means of spectroscopic analysis making use of sophisticated and elaborate spectral analysis. This can for example be realized by imaging the entire spectrum on a CCD camera and by subsequent graphical data processing. Hence, the reference samples allow to calibrate the optical analysis system with respect to broadband fluorescence background which is an important parameter for an accurate and precise analysis of acquired principal components.

In a further embodiment the method comprises the deriving of an at least second parameter of the optical analysis system from an output signal of the detector in the absence of the at least first reference sample and/or in the absence of optical radiation at all. In this case the at least second parameter is representative of system-inherent noise that might be due to the dark current of the detector and general noise that is generated by the optical analysis system itself. Performing the inventive calibration method in the absence of a reference sample effectively allows to determine a calibration value that is due to elastic and inelastic scattering of light inside the optical analysis system. Switching off the light source even allows to determine the dark current of the detector and noise that may be produced by electronic components of the optical analysis system.

In another embodiment the method is applicable to a variety of different reference samples that comprise a reservoir that is at least partially transparent for the excitation radiation of the optical analysis system and for the optical signal emanating from the reference sample and re-entering the optical analysis system. The reservoir may be implemented as a cuvette or a vial and typically comprises the substance that has at least one compound or analyte with a known first concentration. This type of reference sample is preferably applicable to calibrate the optical analysis system with respect to spectroscopic signals representing concentrations of various compounds.

In another embodiment, the reference sample comprises artificial skin tissue with artificial blood vessels. Preferably, the reference sample may comprise various different types of artificial skin tissue that allow to simulate various environmental acquisition conditions. Preferably, this type of reference sample can be used to calibrate the optical analysis system with respect to broadband fluorescence background. Also here, the reference parameters of the artificial skin tissue and the artificial blood vessels are known and can be applied for comparison with corresponding parameters obtained by the multivariate optical analysis. This type of reference sample represents a realistic application scenario when the optical analysis system is implemented as e.g. a non-invasive blood analysis system. In particular, shifting of the volume of interest either into an artificial blood vessel or into neighboring artificial tissue allows to calibrate the optical analysis system either with respect to concentration determination of compounds or with respect to determination of broadband fluorescence background.

In another embodiment the method comprises the further steps of calibrating the optical analysis system by means of the calibration value and repeatedly deriving at least a third parameter of the first reference sample by making use of the at least one principal component. Based on this third parameter that is obtained after calibration of the optical analysis system, a comparison with the at least first reference parameter can be repeatedly performed in order to provide a feedback of the quality of the performed calibration procedure. Thereafter, based on the result of the repeated comparison, a decision can be made whether to retain the calibration value or to discard the performed calibration and to repeat the entire calibration procedure, e.g. by making use of another reference sample.

The calibration of the optical analysis system can be performed in a plurality of different ways, e.g. by specifying a calibration function that makes use of one or more calibration values. The mathematical form of this calibration function depends on the multivariate analysis procedure and on the type of calibration value.

In another embodiment the method of calibrating further comprises recognizing the at least first reference sample by means of an imaging system and by means of a reference mark that is specific to the at least first reference sample and that is typically attached to the reference sample. By means of the imaging system and the reference mark, the reference sample can be automatically identified by means of the optical analysis system. By making use of this recognition or identification the at least first reference parameter of the identified reference sample can be obtained from a storage that provides assignment between reference samples and their associated reference parameters. Hence, the optical analysis system reaches a high degree of automation and thus enables a highly automated calibration procedure that may be triggered by an unskilled user, simply by inserting a specific reference sample into the optical analysis system.

In another aspect the invention provides a computer program product for calibrating an optical analysis system. The optical analysis system is able to determine an amplitude of a principal component of an optical signal by making use of a multivariate optical element and a detector. The computer program product is executable by means of a processing unit of the optical analysis system and is operable to determine the at least one principal component of at least one optical signal that is obtained from at least a first reference sample and to derive at least a first parameter of a first reference sample by making use of the at least one principal component. Further, the computer program product is operable to perform a comparison between the at least first parameter with at least a first reference parameter of the reference sample and to determine at least a first calibration value for the at least first parameter by making use of the comparison. This at least first calibration value can further be applied by the computer program product for calibrating the optical analysis system. In this context the parameters and reference parameters may correspond to various properties of the reference samples. For instance, a reference parameter may represent a concentration of a certain compound or analyte of a substance of the reference sample or it may refer to background noise of the optical signal that corresponds to a spectroscopic signal acquired from the reference sample.

In another aspect the invention provides an optical analysis system that is adapted to determine an amplitude of a principal component of an optical signal by making use of a multivariate optical element and a detector. The optical analysis system comprises means for determining the at least one principal component of at least one optical signal that is obtained from at least a first reference sample and means for deriving at least a first parameter of the first reference sample by making use of the at least one principal component. Further, the optical analysis system comprises means for performing a comparison between the at least first parameter with at least a first reference parameter of the reference sample and means for determining at least a first calibration value for the at least first parameter by making use of the comparison. This at least first calibration value is further applicable for calibrating the optical analysis system.

In a preferred embodiment the optical analysis system further comprises storage means for storing the at least first reference parameter of the at least first reference sample in the form of an assignment between the at least first reference sample and the at least first reference parameter. In this way the at least first reference parameter of a reference sample can be obtained from the storage means for comparison with the at least first parameter that is actually determined by the optical analysis system. Preferably, the storage means are also adapted to store the generated calibration values.

In another aspect the invention provides an optical analysis system that is adapted to determine an amplitude of a principal component of an optical signal by making use of a multivariate optical element and a detector. The optical analysis system comprises an analysis unit for determining at least one principal component of at least one optical signal that is obtained from at least a first reference sample and for deriving at least a first parameter of the first reference sample by making use of the at least one principal component. Further, the optical analysis system comprises a calibration unit for performing a comparison between the at least first parameter with at least a first reference parameter of the reference sample and for determining at least a first calibration value for the at least first parameter by making use of the comparison. This at least first calibration value is applicable for calibrating the optical analysis system.

In another embodiment the optical analysis system further comprises an imaging system that is adapted to provide a visual image of the at least first reference sample has a reference mark. Further, the optical analysis system comprises a reference sample identification unit that is adapted to recognize or to identify the at least first reference sample by means of the output of the imaging system. The sample identification unit is further adapted to provide information of a recognized sample to the calibration unit in response to a recognition of the at least first reference sample.

In still another aspect the invention provides a set of reference samples for calibrating an optical analysis system that is adapted to determine an amplitude of a principal component of an optical signal by making use of a multivariate optical element and a detector. The reference samples of the set of reference samples are at least partially transparent for an excitation radiation of the optical analysis system and for the optical signal emanating from a volume of interest inside the reference sample and re-entering the optical analysis system. The reference samples comprise a substance that has at least one compound or analyte and further comprises data that is related to the concentration of the at least one compound or analyte of the substance. This data may either be obtained by means of sophisticated and elaborate spectral analysis of the substance or by designing the substance in a well defined way.

It is further to be noted that any reference signs in the claims are not to be construed as limiting the scope of the present invention.

BRIEF DESCRIPTION OF THE DRAWINGS

In the following, preferred embodiments of the invention will be described in detail by making reference to the drawings in which.

DETAILED DESCRIPTION OF THE PRESENT SYSTEM

Figure 1:
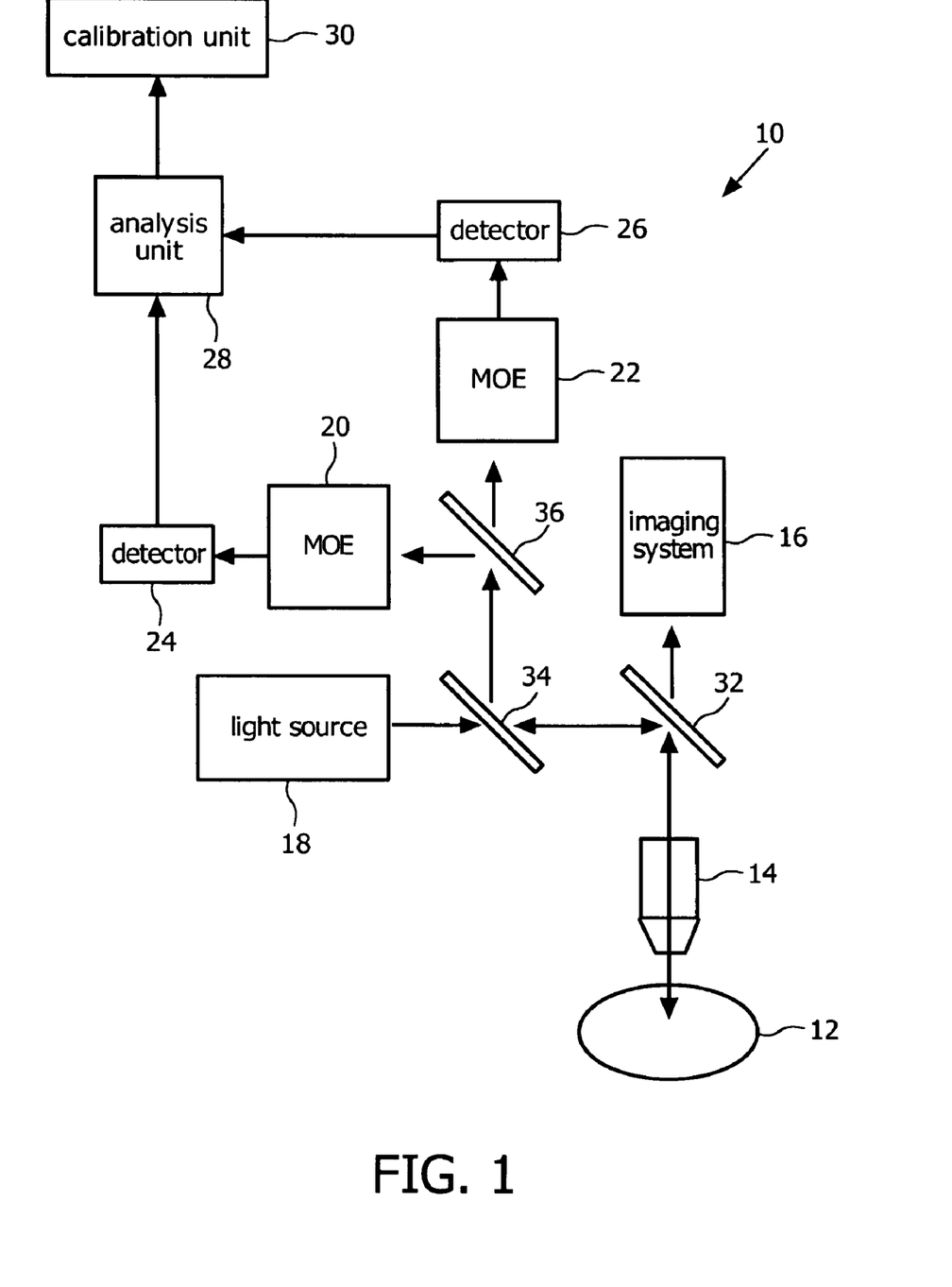
FIG. 1 shows a block diagram of the inventive optical analysis system.

FIG. 1 shows a block diagram of the optical analysis system 10 that is designed for e.g. in-vivo non-invasive analysis of biological tissue or biological substances, like blood flowing underneath the surface of a person's skin. The optical analysis system 10 has an objective lens 14, a light source 18, an imaging system 16 and spectroscopic analysis means comprising multivariate optical elements (MOE) 20, 22, detectors 24, 26, an analysis unit 28 and a calibration unit 30. Excitation radiation that is generated by the light source 18, which is typically implemented as a laser light source emitting radiation in the infrared or near-infrared range, is directed and focused on a sample 12 by means of dichroic mirrors 34, 32 and the focusing lens 14. The light may be focused on e.g. a blood vessel by using an imaging and analysis system as described in the international patent application WO 02/057759.

Inside the sample 12 the excitation radiation is typically subject to various scattering processes including elastic scattering leading to a broadband fluorescence background and inelastic scattering processes, like Stokes or anti-Stokes scattering processes leading to well defined Raman peaks in the spectrum of the scattered radiation. Scattered radiation that re-enters the objective lens 14 is filtered by means of the dichroic mirrors 32, 34 in order to selectively direct Raman shifted radiation to the beam splitter 36 that distributes the spectroscopic signal to both MOEs 20, 22.

Typically, MOEs 20, 22 are implemented by means of a combination of a dispersive optical element and a filter featuring a spatial transmission function that corresponds to a weighting function that serves to extract the principal component from the spectroscopic signal. For instance MOE 20 corresponds to the negative part of the spectral weighting function and MOE 22 corresponds to the positive part of the spectral weighting function. Both MOEs 20, 22 provide a light intensity that can be separately detected by means of the detectors 24 and 26 that are typically implemented as photodiodes since they do not have to provide a spatial resolution. Both detector outputs are coupled to the analysis unit 28 that is adapted to generate the principal component of the acquired spectroscopic signal. Further, the analysis unit 28 may also be adapted to assign the principal component to a concentration of a compound or analyte of a substance of the sample 12.

The calibration unit 30 is adapted to compare the principal component and/or the determined compound concentration with corresponding reference values of the sample 12. Whenever a measured concentration provided by the analysis unit 28 deviates from a corresponding reference value that is stored in the calibration unit 30, the calibration unit generates a calibration value for this specific compound and uses this calibration value when the optical analysis system 10 is used for determination of compound concentrations of unknown samples. Hence, by means of the calibration value a systematic error-prone concentration determination of the optical analysis system can be compensated. The calibration procedure can be performed with respect to various different analytes and compounds of a single reference sample 12 by making use of different multivariate optical elements 20, 22 or by making use of MOEs 20, 22 that are reconfigurable and thus provide spectral analysis of an optical signal with respect to different compounds and analytes.

The calibration performed by the optical analysis system 10 is by no means limited to a calibration of signals representing principal components or concentrations of analytes. Moreover, the analysis unit 28 and calibration unit 30 are also adapted to calibrate the optical analysis system with respect to e.g. a broadband fluorescence background and system-inherent noise that is either obtained from a reference sample 12 or that is generated by the optical analysis system itself. System-inherent noise that might be due to dark currents of the detectors 24, 26 and/or scattering of optical signals even in the absence of the sample 12 can also be classified by generating a corresponding calibration value that is preferably stored in the calibration unit and that can later on be used for eliminating or at least minimizing an impact of these parasitic defects.

The reference sample 12 may represent artificial skin with blood vessels. The substance may be one or more of the following analytes: glucose, lactate, cholesterol, oxy-hemoglobin and/or desoxy-hemoglobin, glycohemoglobin (HbA1c), hematocrit, cholesterol (total, HDL, LDL), triglycerides, urea, albumin, creatinin, oxygenation, pH, bicarbonate and many others. In normal mode, the concentrations of these substances is to be determined from unknown samples in a non-invasive way using optical spectroscopy.

The reference sample 12 can be realized in a variety of different ways, e.g. as a cuvette filled with an aqueous liquid serving as a solvent for compounds or analytes to be measured by the optical analysis system 10. The reference sample 12 may comprise even a large amount of dissolved compounds and analytes whose spectra are preferably not correlated. When designing a reference sample 12 with various compounds, it is advantageous to make use of such components that show clearly distinctive spectra. Typically, those compounds whose spectra show a certain similarity shall not be combined in a single reference sample in order to guarantee a non-ambiguous spectral analysis. The composition of the samples or the set of samples may be designed with respect to the intended application scenario of the optical analysis system.

When for instance the system is only dedicated for determining the concentration of glucose in e.g. blood, it is sufficient to provide a reference sample having a well known concentration of glucose that is dissolved in an aqueous liquid having the same or at least similar optical properties compared to blood. In other application scenarios, where the optical analysis system is dedicated to determine concentrations of various different compounds and analytes, the composition of a reference sample or a set of reference samples has to take into account the similarity or correlation of the spectra of these compounds or analytes. Preferably, the samples are designed in such a way that each sample provides as many compounds or analytes as possible in order to keep the total number of different reference samples as small as possible. Additionally, the total number of reference samples might be governed by a predefined and required accuracy of the concentration determination performed by the optical analysis system. Generally, the more reference samples are used for calibration the better the calibration and the precision of the optical analysis system will be.

The imaging system 16 provides a visual image of at least a volume of interest inside the sample 12 to which the excitation radiation generated by the light source 18 is directed. By means of the imaging system 16 a sample 12 comprising artificial skin and artificial blood vessels can be effectively used for calibration purpose. For instance, by monitoring of the excitation beam that is focused on an artificial blood vessel, the imaging system 16 may provide information to the analysis unit 28 and calibration unit 30 that the detected signals correspond to an artificial blood vessel that is specified by means of at least one reference parameter which can be used for the calibration procedure. In the same way the imaging system 16 may provide information when e.g. the excitation radiation is focused on skin tissue in the vicinity of a blood vessel. In this case information is obtained that the acquired optical signals correspond to a sample that gives mainly rise to a broadband fluorescence background. In this case the optical analysis system can be calibrated with respect to a fluorescence signal which is advantageous for precise and reliable spectral analysis.

Furthermore, the imaging system 16 can be used in order to recognize or to identify samples of different type that comprise a mark. The mark typically represents an identification code of the sample and allows an automatic sample identification. In response to an automatic identification of a sample, the calibration unit 30 is enabled to extract corresponding reference parameters from a memory in an autonomous way. This functionality of autonomous sample recognition provides a high degree of automation of the optical analysis system and allows, that even an unskilled user of the optical analysis system can trigger a calibration procedure when required.

Figure 2A:
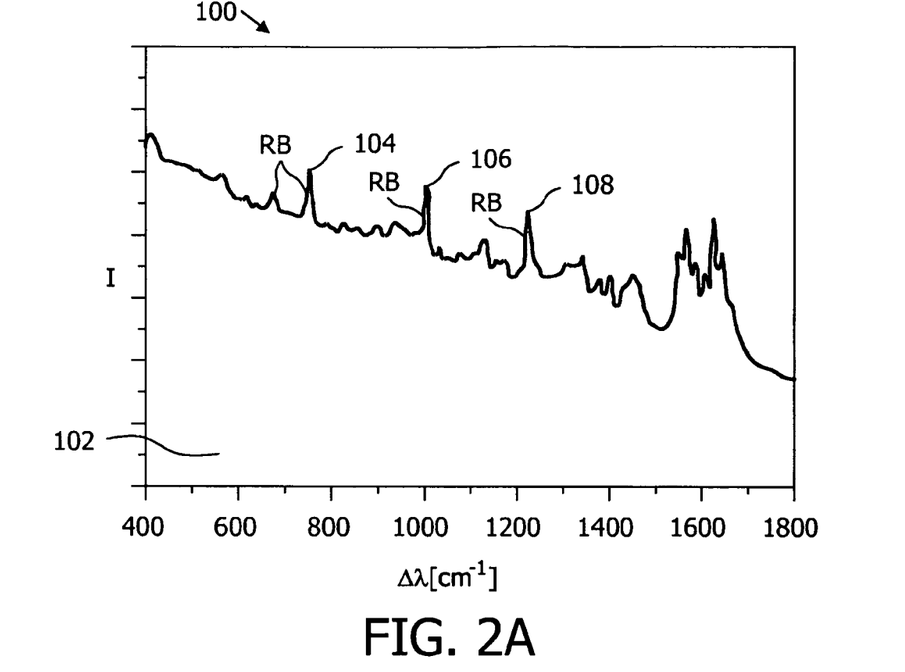
FIGS. 2a & 2b are spectra of the optical signal generated from blood in the skin and from a sample comprising one analyte in a solution.
Figure 2B:
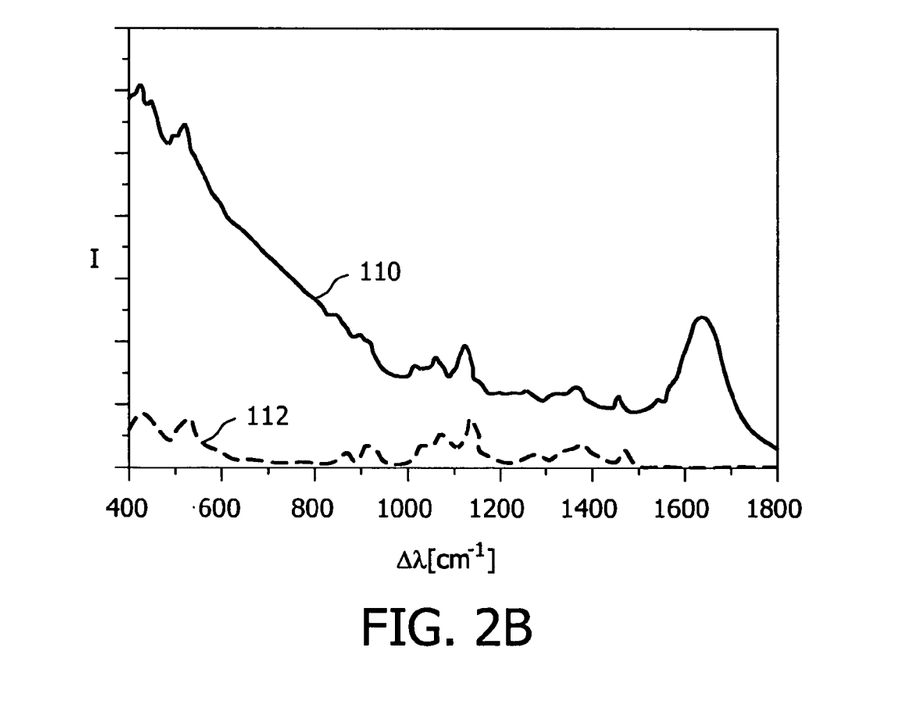

A spectrum 100 of the optical signal generated in this way is shown in FIG. 2A. The spectrum comprises a relatively broad fluorescence background (FBG) 102 and relatively narrow Raman bands (RB) 104, 106, 108. The x-axis of FIG. 2A denotes the wavelength shift with respect to the 785 nm of the excitation by light source 18 in wave numbers. The y-axis of FIG. 2A denotes the intensity in arbitrary units. The x-axis corresponds to zero intensity. The wavelength and the intensity of the Raman bands, i.e. the position and the height, is indicative for the type of analyte as is shown in the example of FIG. 2B for the analyte glucose which was dissolved in a concentration of 80 mMol in water. The solid line 110 of FIG. 2B shows the spectrum of both glucose and water, the dashed line 112 of FIG. 2B shows the difference between the spectrum of glucose in water and the spectrum of water without glucose. The amplitude of the spectrum with these bands is indicative of the concentration of the analyte.

Figure 3:
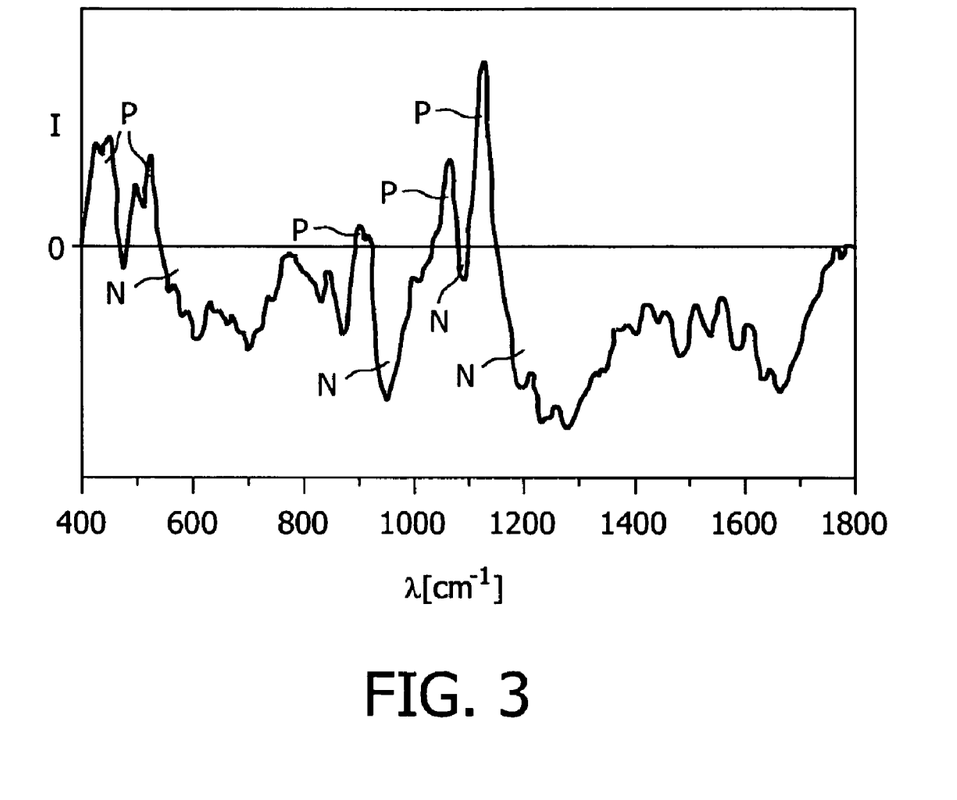
FIG. 3 shows a spectral weighting function implemented in a multivariate optical element.

Because blood comprises many compounds each having a certain spectrum which may be as complex as that of FIG. 2B, the analysis of the spectrum of the optical signal is relatively complicated. Via the MOE 20,22, the optical signal is sent to the analysis unit. The weighing of the optical signals by means of a weighting function is schematically shown e.g. in FIG. 3. The weighting function of FIG. 3 is designed for glucose in blood. It comprises a positive part P and a negative part N. The positive part P and the negative part N each comprise in this example more than one spectral band.

Figure 4:
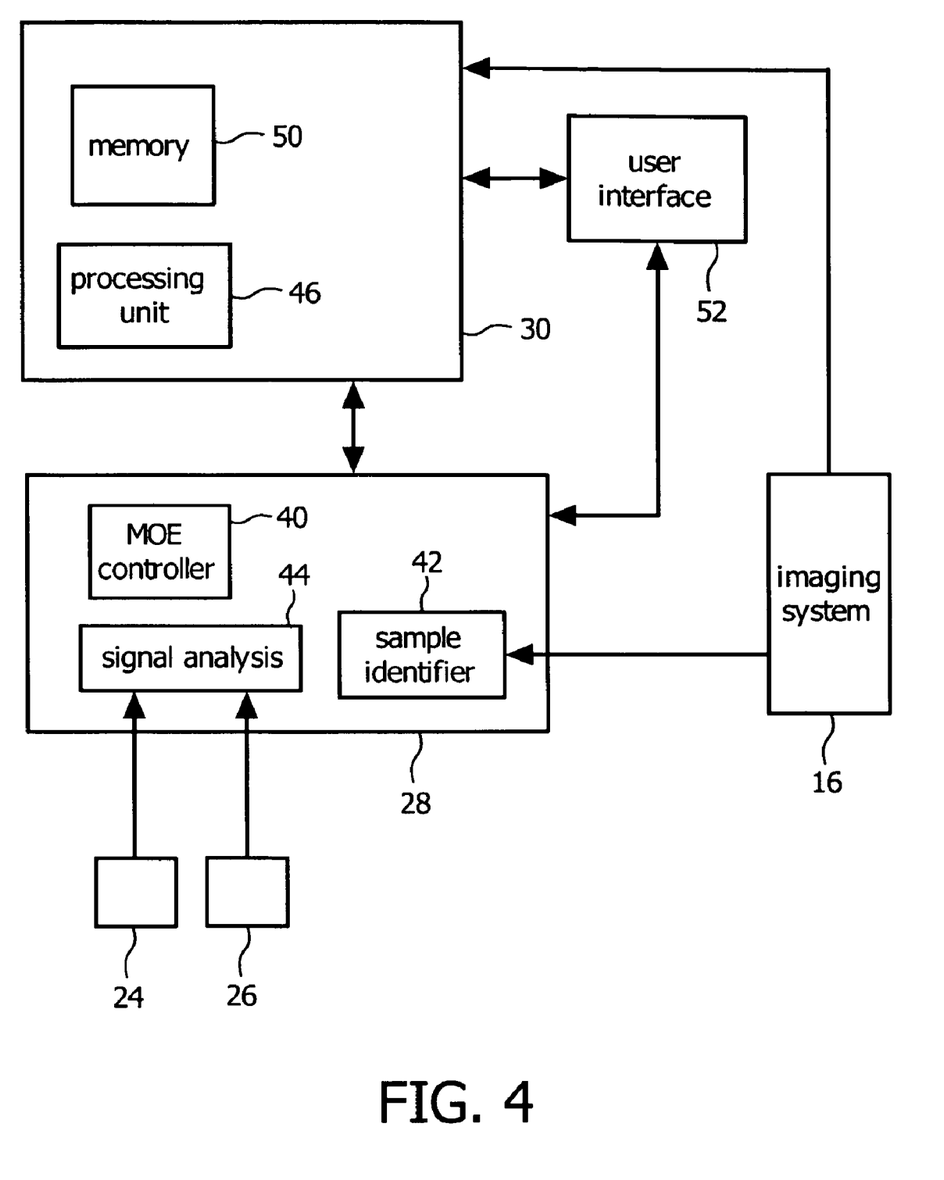
FIG. 4 shows a detailed block diagram of the analysis unit and calibration unit of the optical analysis system.

FIG. 4 shows a detailed block diagram of the analysis unit 28 and the calibration unit 30 of the optical analysis system 10. The two detectors 24, 26 are coupled to the analysis unit 28 providing positive and negative parts of the principal component for determination of the concentration of a particular compound or analyte. The analysis unit has a signal analysis module 44, a controller 40 for controlling the multivariate optical elements 20, 22 as well as a sample identification module 42. The calibration unit 30 has a memory 50 as well as a processing unit 46. Further, calibration unit 30 and analysis unit 28 are coupled to a user interface 52 and to the imaging system 16.

The signal analysis module 44 of the analysis unit 28 is adapted to process the output of the two detectors 24, 26 in order to generate the principal component being representative of the concentration of a particular compound or analyte. The MOE controller is only of relevance when the two MOEs 20, 22 are implemented as reconfigurable multivariate optical elements. For instance, the MOEs might be realized by a grating and a reconfigurable spatial transmission pattern, e.g. a tunable liquid crystal cell sandwiched between crossed polarizers. By means of the MOE controller 40 and a reconfigurable MOE 20, 22, the optical analysis or spectral analysis can be selectively performed with respect to different compounds of the sample. For each compound, the MOE 20, 22 has to be reconfigured in order to represent a compound specific spectral weighting function.

The imaging system 16 is adapted to generate a visual image of either a volume of interest within the sample 12 or to provide a visual image of a reference mark of the sample to the sample identification module 42. The sample identification module 42 is provided with imaging processing means in order to recognize or to identify a specific classified reference sample. Upon identification of a sample, the sample identification module 42 provides the sample information to the calibration unit 30. The calibration unit 30 in turn makes use of this sample identification information for accessing corresponding reference parameters of the respective sample from the memory 50. The processing unit 46 is adapted to compare the reference values stored in the memory 50 with corresponding values obtained from the signal analysis 44 and applied to the calibration unit 30. In case of a mismatch between data obtained by an actual measurement and data acquired from the memory 50, the processing unit 46 derives and calculates a respective calibration value. Typically, such calibration values are also stored in the memory 50 in a separate memory block and they are used either by the processing unit 46 or by the signal analysis module 44, when the optical analysis system 10 is in normal operation mode and has to provide reliable and precise information of e.g. concentration of analytes of unknown samples.

The user interface 52 provides interaction with a user of the optical analysis system. The user interface 52 may display actual measured concentrations determined by e.g. the signal analysis module 44 and may also be used for an interactive calibration procedure. For instance, the user interface 52 may instruct the user to place a distinct reference sample into the optical analysis system 10. Then, the system may autonomously perform a calibration procedure that may provide the user with relevant calibration information. In particular, when the system determines a calibration value, successively performs a calibration procedure and repeatedly checks whether the calibration has been successful and determines an unacceptable precision of the result, the user might be informed that the optical analysis system is currently subject to a severe malfunction.

Moreover, by means of the user interface 52, the calibration procedure can be performed in an interactive manner. Instead of an automatic recognition of a reference sample, the user may also manually enter an identification code of a reference sample and in case that relevant data of this reference sample is not stored in the memory 50, the user may also provide the relevant calibration information that is needed in order to perform the calibration and that may for future applications be stored in the memory 50.

Figure 5:
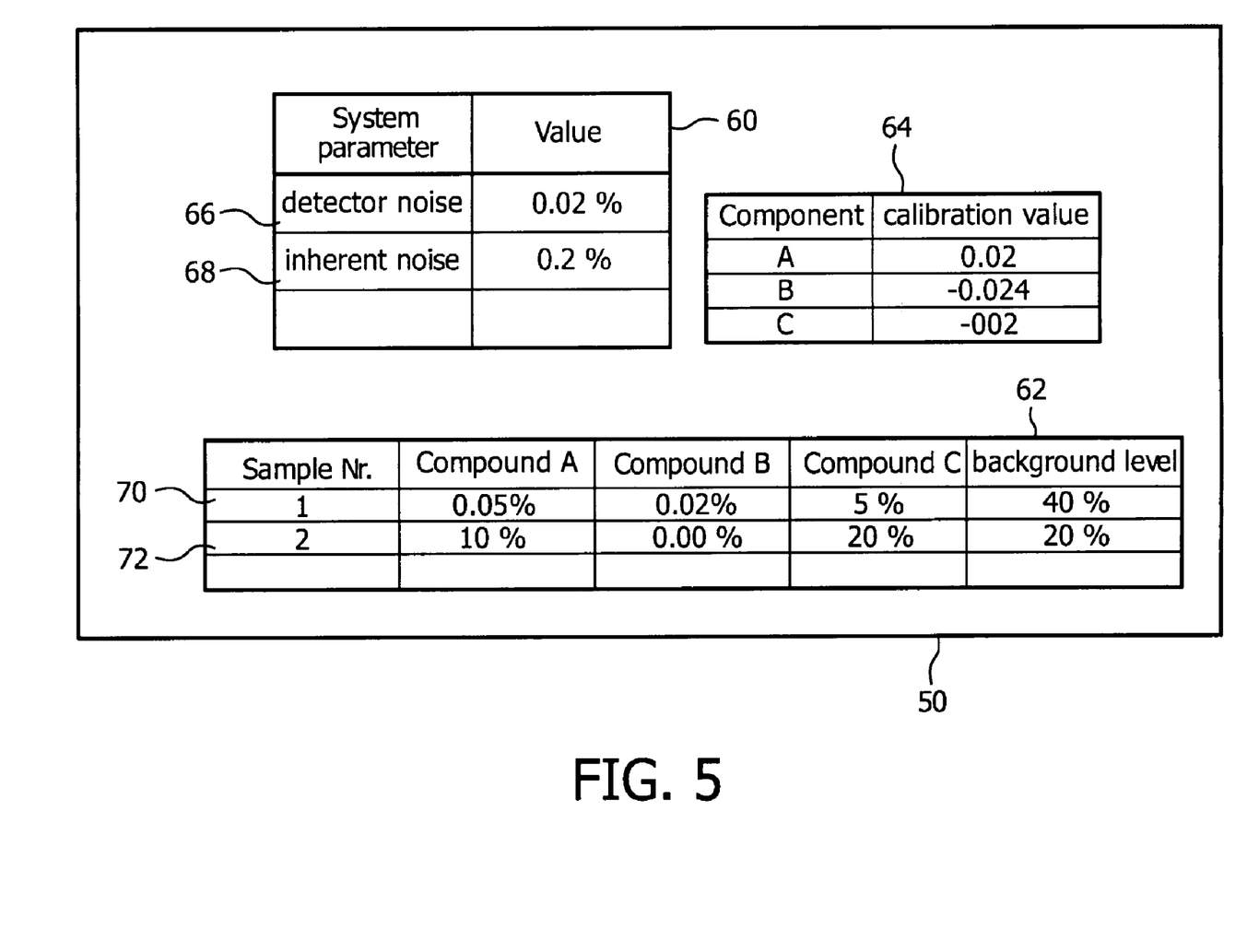
FIG. 5 shows a block diagram of the internal structure of the memory.

FIG. 5 illustrates an example of an internal structure of the memory 50. Here, the memory 50 provides at least three different memory blocks denoted system table 60, reference sample table 62 and calibration table 64. The reference sample table 62 provides information of the composition of various samples. This information is either obtained by a high-precision spectroscopic analysis or by means of a well-known design and manufacturing of the sample. For instance, a sample denoted sample number 1 and illustrated in row 70 has three components, namely A, B and C of 0.05%, 0.02% and 5%, respectively. Further, sample number 1, 70, is specified with a background level of 40%. This background level information allows to calibrate the optical analysis system 10 not only with respect to signal amplitudes but also with respect to the level of background noise. Sample number 2 illustrated in row 72 is stored in a similar way.

The system table 60 specifies system-inherent noise parameters that can be obtained in the absence of a sample and/or in the absence of radiation. For instance row 66 represents the detector noise of 0.02% that might be due to the dark current of the detectors 24, 26 and row 68 may represent other system-inherent noise that might be e.g. due to fluorescence. In the normal operation mode these system parameters stored in the system table 60 have to be taken into account for all measurements performed with the optical analysis system.

The calibration table 64 can be used to store calibration values that have been determined by means of the inventive calibration method. These calibration values are preferably determined by comparison with the reference values provided by the reference sample table 62 with values that are determined by the optical analysis system. The calibration table 64 provides an assignment between various components A, B and C to respective calibration values that are needed to calibrate and to scale the output of the signal analysis to a precise value.

The various entries of the tables 60, 62, 64 as well as the scale of the relevant parameters can be performed in any arbitrary way. For instance, reference sample table may also refer to an amplitude or intensity of the principal component or the positive and negative part of the principal component instead of a derived compound concentration expressed in percentage.

Figure 6:
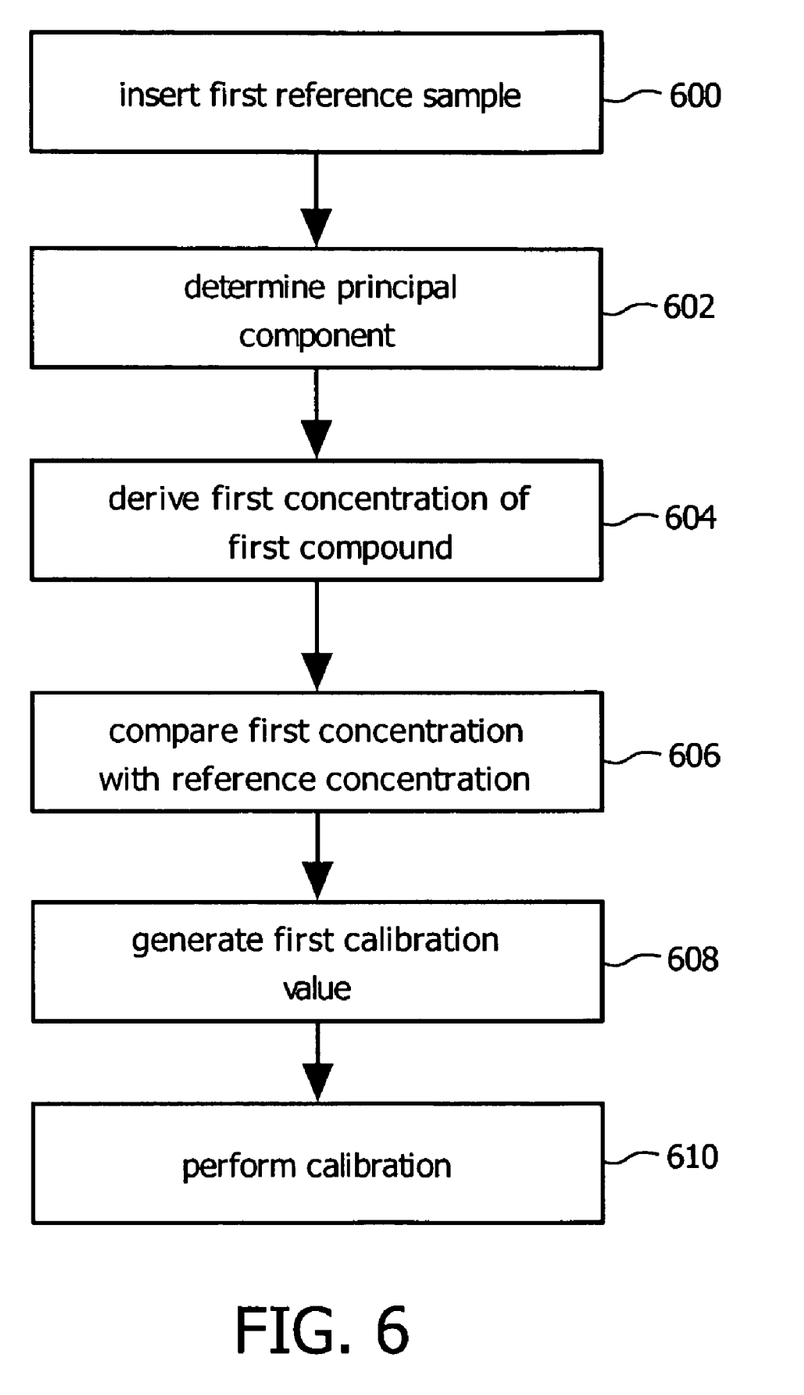
FIG. 6 illustrates a flowchart of calibrating the optical analysis system.

FIG. 6 illustrates a flowchart of performing the inventive calibration procedure. In a first step 600 the reference sample is placed in an optical inspection volume of the optical analysis system. Thereafter, in step 602 excitation radiation is focused on the reference sample and a corresponding optical signal carrying spectroscopic information of the reference sample re-enters the optical analysis system and can be analyzed by means of the multivariate optical elements and detectors in order to determine the principal component of the optical signal. Based on this analysis, at least a first concentration of a first compound or analyte of the reference sample can be derived in step 604 and can be compared with at least a first reference concentration in the subsequent step 606. As a result of this comparison an at least first calibration value can be generated in step 608 that is finally used for a calibration of the entire system that is performed in step 610. Preferably, the calibration procedure can be entirely performed by means of a computer program that is executable by the processing unit 46 of the calibration module 30. In this way the calibration can be repeatedly performed in order to adapt the system to varying environmental condition and to various samples to be spectrally analyzed.

If the MOE of the optical analysis system is implemented as a reconfigurable MOE or if the MOE can be replaced by another MOE being designed for a different compound or analyte, steps 602 through 610 can be repeatedly executed for a different compound and a corresponding different reference parameter. In this way a single reference sample might be used to calibrate the system with respect to different analytes or compounds.

Figure 7:
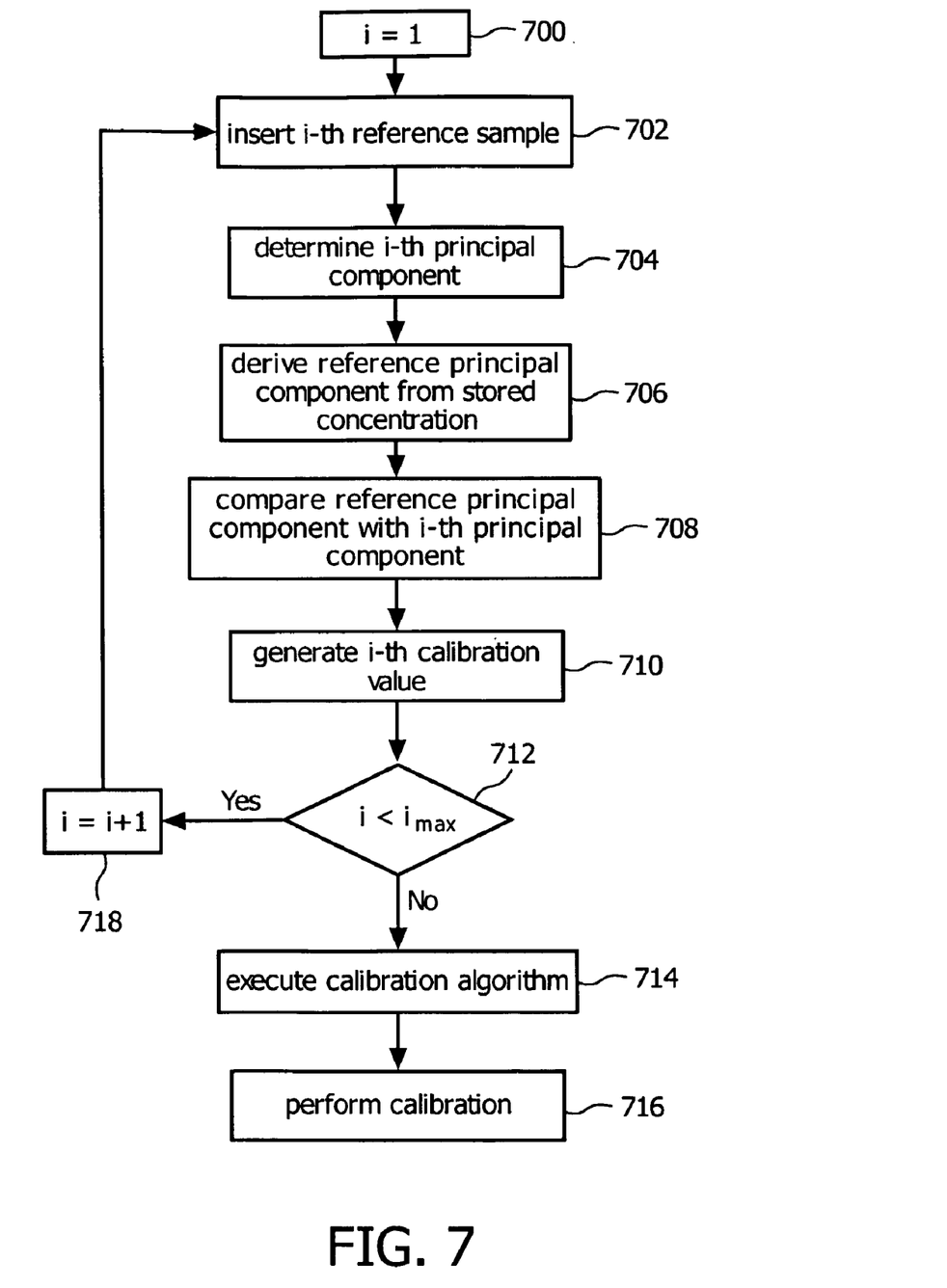
FIG. 7 shows a flowchart of a calibration procedure making use of various reference samples.

FIG. 7 is illustrative of a flowchart of performing a calibration procedure making use of various reference samples. In a first step 700 a reference sample index i is initialized and equals 1. Then, in the following step 702, the first reference sample is placed or inserted into the optical analysis system. In the following steps 704 through 710 a principal component is determined and compared with stored information, a procedure that has a high similarity to the process steps described in steps 602 through 608 of FIG. 6. In step 704 a first principal component of the first reference sample is determined by means of the multivariate optical analysis. Thereafter, a reference principal component is obtained in step 706 either by calculation from a stored concentration of the first reference sample or by means of a readout of the memory 50, if the reference principal component is appropriately stored in the memory 50. Thereafter, in step 708 this reference principal component is compared with the first principal component and in the subsequent step 710, based on this comparison a first calibration value is generated.

In the subsequent step 712, the reference sample index i is compared with a maximum reference index $i_{max}$. If i is smaller than $i_{max}$, the method continues with step 718, where the reference sample index i is incremented by 1. Thereafter, the method returns to step 702 and steps 702 through 710 are repeatedly executed by making use of the second reference sample, by determining the second principal component, comparing second reference principal component with second principal component and generating a second calibration value. This procedure continues as long as the reference sample index i is smaller than $i_{max}$. As soon as the maximum number of execution cycles has been executed, the decision performed in step 712 win be followed by step 714, where a calibration algorithm is executed. The result of the calibration algorithm may be a single or a set of calibration values depending on the number of compounds or analytes for which the various reference samples are representative. After determination of a calibration value or a set of calibration values in step 714 the final step of calibration 716 is executed.

In addition, the section headings included herein are intended to facilitate a review but are not intended to limit the scope of the present system. Accordingly, the specification and drawings are to be regarded in an illustrative manner and are not intended to limit the scope of the appended claims.

LIST OF REFERENCE NUMERALS

- 10 optical analysis system
- 12 sample
- 14 objective lens
- 16 imaging system
- 18 light source
- 20 multivariate optical element (MOE)
- 22 multivariate optical element (MOE)
- 24 detector
- 26 detector
- 28 analysis unit
- 30 calibration unit
- 32 dichroic mirror
- 34 dichroic mirror
- 36 beam splitter
- 40 multivariate controller
- 42 sample identifier
- 44 signal analysis module
- 46 processing unit
- 50 memory device
- 52 user interface
- 60 system table
- 62 reference sample table
- 64 calibration table
- 100 spectrum
- 102 broad fluorescence background
- 104 Raman band
- 106 Raman band
- 108 Raman band
- 110 combined spectrum
- 112 glucose spectrum

The invention claimed is:

1. A method of calibrating an optical analysis system being adapted to determine an amplitude of a principal component of an optical signal by making use of a multivariate optical element and a detector, the method of calibrating comprising the acts of:

determining the principal component of the optical signal being obtained from a first reference sample;
    deriving at least a first parameter of the first reference sample by making use of the principal component;
    performing a comparison between the at least first parameter with at least a first reference parameter of the first reference sample;
    determining at least a first calibration value for the at least first parameter by making use of the comparison, the at least first calibration value being applicable for calibrating the optical analysis system; and
    deriving an at least second parameter of the optical analysis system from an output signal of the detector in absence of the first reference sample and/or in absence of optical radiation, the at least second parameter being representative of system inherent noise and being applicable for calibrating the optical analysis system.

2. The method according to claim 1, wherein the at least first parameter and the at least first reference parameter are representative of a concentration of at least one component of a substance being located inside a volume of interest of the reference sample, and wherein the optical signal is representative of a spectroscopic signal obtained from the volume of interest.

3. The method according to claim 1, wherein the at least first parameter and the at least first reference parameter are representative of a portion of the optical signal that is due to inelastic scattering of optical radiation inside the first reference sample.

4. The method according to claim 1, wherein the reference sample comprising a reservoir being at least partially transparent for an excitation radiation of the optical analysis system and for the optical signal, the reservoir comprising a substance having at least one component with a first concentration.

5. The method according to claim 1, wherein the reference sample comprising artificial skin tissue with artificial blood vessels.

6. The method according to claim 1, further comprising the acts of:

recognizing the first reference sample by an imaging system and by a reference mark being specific for the first reference sample; and
    obtaining the at least first reference parameter of the first reference sample from a storage providing an assignment of the first reference sample and the at least first reference parameter.

7. A method of calibrating an optical analysis system being adapted to determine an amplitude of a principal component of an optical signal by making use of a multivariate optical element and a detector, the method of calibrating comprising the acts of:

determining the principal component of the optical signal being obtained from a first reference sample;
    deriving at least a first parameter of the first reference sample by making use of the principal component;
    performing a comparison between the at least first parameter with at least a first reference parameter of the reference sample;
    determining at least a first calibration value for the at least first parameter by making use of the comparison, the at least first calibration value being applicable for calibrating the optical analysis system;
    calibrating the optical analysis system by the at least a first calibration value;
    repeatedly deriving at least a third parameter of the first reference sample by making use of the principal component; and
    repeatedly performing a comparison between the at least third parameter with the at least first reference parameter of the first reference sample in order to provide a feedback of a quality of the calibration.

8. A computer program product for calibrating an optical analysis system for determining an amplitude of a principal component of an optical signal by making use of a multivariate optical element and a detector, the computer program product being executable by a processing unit of the optical analysis system and being operable to:

determine the principal component of the optical signal being obtained from a first reference sample;
    derive at least a first parameter of the first reference sample by making use of the principal component;

perform a comparison between the at least first parameter with at least a first reference parameter of the first reference sample;

determine at least a first calibration value for the at least first parameter by making use of the comparison, the at least first calibration value being applicable for calibrating the optical analysis system; and derive an at least second parameter of the optical analysis system from an output signal of the detector in absence of the first reference sample and/or in absence of optical radiation, the at least second parameter being representative of system inherent noise and being applicable for calibrating the optical analysis system.

9. An optical analysis system being adapted to determine an amplitude of a principal component of an optical signal by making use of a multivariate optical element and a detector, the optical analysis system comprising:

means for determining the principal component of the optical signal being obtained from a first reference sample;

means for deriving at least a first parameter of the first reference sample by making use of the principal component;

means for performing a comparison between the at least first parameter with at least a first reference parameter of the first reference sample;

means for determining at least a first calibration value for the at least first parameter by making use of the comparison, the at least first calibration value being applicable for calibrating the optical analysis system; and means for deriving an at least second parameter of the optical analysis system from an output signal of the detector in absence of the first reference sample and/or in absence of optical radiation, the at least second parameter being representative of system inherent noise and being applicable for calibrating the optical analysis system.

10. The optical analysis system according to claim 9, further comprising storage means for storing the at least first reference parameter of the first reference sample in form of an assignment between the first reference sample and the at least first reference parameter.

11. An optical analysis system being adapted to determine an amplitude of a principal component of an optical signal by making use of a multivariate optical element and a detector, the optical analysis system comprising:

an analysis unit for determining the principal component of the optical signal being obtained from a first reference sample and for deriving at least a first parameter of the first reference sample by making use of the at least one principal component;

a calibration unit for performing a comparison between the at least first parameter with at least a first reference parameter of the reference sample; for determining at least a first calibration value for the at least first parameter by making use of the comparison, the at least first calibration value being applicable for calibrating the optical analysis system; and for deriving an at least second parameter of the optical analysis system from an output signal of the detector in absence of the first reference sample and/or in absence of optical radiation, the at least second parameter being representative of system inherent noise and being applicable for calibrating the optical analysis system.

12. The optical analysis system according to claim 11, wherein the first parameter and the first reference parameter are representative of a concentration of at least one component of a substance being located inside a volume of interest of the reference sample and wherein the optical signal is representative of a spectroscopic signal obtained from the volume of interest.

13. The optical analysis system according to claim 11 further comprising:

an imaging system being adapted to provide a visual image of the first reference sample having a reference mark; and a sample identification unit being adapted to recognize the first reference sample by the output of the imaging system and being further adapted to provide information of a recognized sample to the calibration unit.

* * * * *

UNITED STATES PATENT AND TRADEMARK OFFICE
CERTIFICATE OF CORRECTION

| | | |
|---|---|---|
| PATENT NO. | : 7,899,636 B2 | Page 1 of 1 |
| APPLICATION NO. | : 11/721368 | |
| DATED | : March 1, 2011 | |
| INVENTOR(S) | : Bernardus Leonardus Gerardus Bakker et al. | |

It is certified that error appears in the above-identified patent and that said Letters Patent is hereby corrected as shown below:

Title page Should read

Item (75) Inventor: Bernardus Leonardus Gerardus Bakker, Eindhoven (NL)

Michael Cornelis Van Beek, Eindhoven (NL)

Wouter Harry Jacinth Rensen, Eindhoven (NL)

Signed and Sealed this
Twentieth Day of September, 2011

David J. Kappos
*Director of the United States Patent and Trademark Office*